US007083798B1

(12) United States Patent
Baxter (10) Patent No.: US 7,083,798 B1
(45) Date of Patent: Aug. 1, 2006

(54) METHOD OF IMMUNOMODULATORY TREATMENT OF INSULIN DEPENDENT DIABETES MELLITUS USING MYCOBACTERIAL CELL WALL COMPOSITIONS (75) Inventor: Alan George Baxter, Annandale (AU)

(73) Assignee: Centenary Institute of Cancer Medicine and Cell Biology, Camperdown (GB)

( * ) Notice: Subject to any disclaimer, the term of this patent is extended or adjusted under 35 U.S.C. 154(b) by 0 days.

(21) Appl. No.: 09/308,192

(22) PCT Filed: Nov. 13, 1997

(86) PCT No.: PCT/AU97/00770

§ 371 (c)(1),
(2), (4) Date: Jul. 14, 1999

(87) PCT Pub. No.: WO98/20900

PCT Pub. Date: May 22, 1998

(30) Foreign Application Priority Data

Nov. 13, 1996 (AU) .................................. PO3593

(51) Int. Cl.
A61K 45/00 (2006.01)
A61K 47/00 (2006.01)
A61K 38/16 (2006.01)
A61K 39/02 (2006.01)
A61K 39/04 (2006.01)

(52) U.S. Cl. ............................... 424/282.1; 424/279.1; 424/278.1; 424/234.1; 424/248.1; 514/866; 514/8; 514/12

(58) Field of Classification Search ............. 424/278.1, 424/282.1, 234.1, 248.1, 279.1; 514/12, 514/8, 866; 426/279.1
See application file for complete search history.

(56) References Cited

U.S. PATENT DOCUMENTS

| 4,152,423 A | 5/1979 | Adam et al. ................... 424/92 |
| 4,307,229 A | 12/1981 | Liav et al. ................... 536/119 |
| 4,877,612 A * | 10/1989 | Berger et al. ................. 424/92 |

FOREIGN PATENT DOCUMENTS

| GB | 2120548 A | 12/1983 |
| WO | WO 85/05034 * | 11/1985 |
| WO | WO-87/02249 A | 4/1987 |
| WO | WO 91/02542 * | 3/1991 |
| WO | WO-94/16727 A | 8/1994 |
| WO | WO-96/00579 A | 1/1996 |
| WO | WO-96/26288 A | 8/1996 |

OTHER PUBLICATIONS

Qin et al J Immunol. 150 (5), 2072-80, 1993.*
Robinson et al J Clin Lab Immunol. 24 (4), 171-6, 1987.*
Stosic-Grujicic et al. Mikrobiolojija 33 (1): 27-36, 1996.*
Chugh et al. Folia Microbiol. 37: 407-412, 1992.*
Hirschfield et al. (Feb. 1990) "Peptidoglycan-Associated Polypeptides of Mycobacterium Tuberculosis," *J. Bacteriol.* 172(2): 1005-1013.
Azuma et al. (Nov. 1968) "Fractionation of Mycobacterial Cell Wall," *J. Bacteriol.* 96(5): 1885-1887.
Baxter et al. (1994) "Mycobacteria Precipitate an SLE-like Syndrome in Diabetes-Prone NOD Mice," *Immunology* 83: 227-231.
Sadelain et al. (May 1990) "Prevention of Type I Diabetes in NOD Mice by Adjuvant Immunotherapy," *Diabetes* 39(5), 583-587.
Harada et al. (1990) "Prevention of Overt Diabetes and Insolitis in NOD Mice by a Single BCG Vaccination," *Diabetes Res. Clin. Pract.* 8: 85-89.
Beaudet et al. (1983) "Stimulation of Non-Specific Anti-Tumor Resistance in the Mouse Using Cell Wall Preparations from Four BCG Substrains," *Ann. Immunol. (Paris)* 134C(2): 215-226.
Dockrell et al. (Oct. 1996) "Induction of Th1 Cytokine Responses by Mycobacterial Antigens in Leprosy," *Infect. Immun.* 64(10): 4358-4389.
McNeil et al. (Oct. 1996) "Evidence for the Nature of the Link Between the Arabinogalactan and Peptidoglycan of Mycobacterial Cell Walls," *J. Biol. Chem.* 265(30): 18200-18206.
Barnes et al. (Apr. 1992) "Tumour Necrosis Factor Production in Patient with Leprosy," Infect. Immun. 60(4): 1441-1446.

(Continued)

Primary Examiner—S. Devi
(74) Attorney, Agent, or Firm—Morrison & Foerster LLP (57) ABSTRACT The present invention relates generally to a method of immunomodulating therapy and pharmaceutical compositions useful for same. More particularly, the present invention provides a method of ameliorating the effects of autoimmune conditions. Even more particularly, the present invention contemplates a method for preventing, delaying onset of or otherwise ameliorating the effects of insulin-dependant diabetes mellitus (IDDM) by administering a cell wall subunit or a chemical or functional equivalent thereof from *Mycobacterium* or a related organism or other suitable biological source. The present invention is further directed to a pharmaceutical composition useful in preventing, delaying onset of, curing, curing in association with islet replacement or otherwise ameliorating the effects of autoimmune conditions such as IDDM or for enhancing an immune response against melanoma or other cancer comprising a cell wall subunit or a chemical or functional equivalent thereof from *Mycobacterium* or a related organism or other suitable biological source. The cell wall subunit is preferably mycolyl-arabinogalactan-peptidoglycan (MAPG) or a component thereof.

4 Claims, 4 Drawing Sheets

OTHER PUBLICATIONS

Hayashi, Akira (1994) "Interferon-y as a Marker for the Effective Cancer Immunotherapy with BCG-Cell Wall Skeleton," *Proc. Japan Acad* 70(10): 205-209.

Chin et al. (1996) "Mycobacterium Cell Wall: An Alternative to Intravesical Bacillus Calmette Guerin (BCG) Therapy in Orthotopic Murine Bladder Cancer," *Journal of Urology* 156: 1189-1193.

Morales et al. (May 1995) "Immunotherapy of an Experimental Adenocarcinoma of the Prostate," *Journal of Urology* 153: 1706-1710.

Gray et al. (1975) "Brief Communication: Immunotherapy of Cancer: Tumor Suppression And Regression by Cell Walls of Mycobacterium Phiel Attached to Oil Droplets," *Journal of the National Cancer Institute* 55(3): 727-730.

Schultz et al. (1995) "Effect of DETOX as an Adjuvant for melanoma Vaccine," *Vaccine* 13(5): 503-508.

Shehadah et al. (Mar. 1994) "Effect of Adjuvant Therapy on Development of Diabetes in Mouse and Man," *The Lancet* 343: 706-707.

Gazda et al. (Oct. 1996) "Regulation of Autoimmune Diabetes: Characteristics of Non-Islet-Antigen Specific Therapies," *Immunology and Cell Biology* 74(5): 401-407.

Partial European Search Report directed to Counterpart EP Application No. 97911956.

European Office Action mailed Feb. 2, 2006, directed to counterpart EP Application No. 97911956.7

* cited by examiner

FIGURE 7 ns, the percent-
METHOD OF IMMUNOMODULATORY TREATMENT OF INSULIN DEPENDENT DIABETES MELLITUS USING MYCOBACTERIAL CELL WALL COMPOSITIONS

FIELD OF THE INVENTION

The present invention relates generally to a method of immunomodulating therapy and pharmaceutical compositions useful for same. More particularly, the present invention provides a method of ameliorating the effects of autoimmune conditions. Even more particularly, the present invention contemplates a method for preventing, delaying onset of or otherwise ameliorating the effects of insulin-dependent diabetes mellitus (IDDM) by administering a cell wall subunit or a chemical or functional equivalent thereof from *Mycobacterium* or a related organism or other suitable biological source. The present invention is further directed to a pharmaceutical composition useful in preventing, delaying onset of, curing, curing in association with islet replacement or otherwise ameliorating the effects of autoimmune conditions such as IDDM or for enhancing an immune response against melanoma or other cancer comprising a cell wall subunit or a chemical or functional equivalent thereof from *Mycobacterium* or a related organism or other suitable biological source.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Bibliographic details of the publications numerically referred to in this specification are collected at the end of the description.

BACKGROUND OF THE INVENTION

Insulin-dependent diabetes mellitus (IDDM) is a debilitating, chronic, cell-mediated autoimmune disease characterised by lymphocytic infiltration of the pancreatic islets and T lymphocyte-mediated mediated destruction of insulin-producing β cells (1, 2).

Non-obese diabetic (NOD) mice are a valuable model in studying IDDM as they spontaneously develop the disease which has many immunological and pathological similarities to human IDDM (3, 4).

It has been previously shown that administration of Freund's complete adjuvant (CFA) or *Mycobacterium bovis* (*Bacillus* Calmette-Guerin (BCG) [3]) prevents development of diabetes in NOD mice (5, 6). However, Baxter et al (7) showed the administration of BCG, although preventing diabetes in NOD mice, precipitated a syndrome similar to systemic lupus erythematosus (SLE), precluding its use in humans.

In accordance with the present invention, it has been shown that a subunit complex from the cell wall of *Mycobacterium* prevents diabetes in NOD mice without risk of precipitating SLE. The subunit complex, or one or more of its components, are useful, therefore in immunomodulatory therapy for autoimmune diseases and for enhancing an immune response to various cancers.

SUMMARY OF THE INVENTION

One aspect of the present invention contemplates a method of immunomodulatory therapy in a mammal said method comprising administering to said mammal an immunomodulating effective amount of one or more components of the cell wall of *Mycobacterium* or a related organism or analogous components from another biological source.

Another aspect of the present invention provides a method of preventing, delaying onset of, curing or otherwise ameliorating the effects of an autoimmune disease in a mammal said method comprising administering to said mammal an autoimmune-preventing effective amount of one or more components of the cell wall of *Mycobacterium* or a related organism or analogous components from another biological source.

Still another aspect of the present invention is directed to a method of preventing, delaying onset of, curing or otherwise ameliorating the effects of insulin-dependent diabetes mellitus (IDDM) in a mammal said method comprising administering to said mammal an autoimmune-preventing effective amount of one or more components of the cell wall of *Mycobacterium* or a related organism or analogous components from another biological source.

Yet another aspect of the present invention contemplates a method of enhancing an immune response against melanoma or other cancer in a mammal said method comprising administering to said mammal an immunomodulatory effective amount of one or more components of the cell wall of *Mycobacterium* or a related organism or analogous components from another biological source.

Still yet another aspect of the present invention contemplates immunomodulatory therapy in a mammal said method comprising administering to said mammal an immunomodulatory effective amount of mycolyl-arabinogalactan-peptidoglycan (MAPG) or a component thereof with or without other associated cell wall components and submolecular components from a *Mycobacterium* species such as but not limited to *Mycobacterium bovis* or a chemical equivalent of said MAPG or of a component thereof.

Even yet another aspect of the present invention contemplates a method for isolating components of MAPG for use in a therapeutic composition for preventing, delaying the onset of or otherwise ameliorating the effects of diabetes in a mammal or for use in immunomodulatory therapy said method comprising preparing cell envelopes from a species of *Mycobacterium* or related organism or other suitable biological source, subjecting said cell envelopes to glycolipid removing means to remove soluble glycolipids, treating the product so obtained to break the mycolic acids linkage and isolating said mycolic acids, treating the remaining complex to cleave linkage at rhamnose residue connecting arabinogalactan to the peptidoglycan backbone and separating and isolating arabinogalactan and peptidoglycan.

Another aspect of the present invention provides a composition of matter comprising MAPG or a derivative or a component thereof or its derivative.

Yet another aspect of the present invention relates to the use of a cell wall component of *Mycobacterium* in immunomodulatory therapy.

BRIEF DESCRIPTION OF THE FIGURES

In the Figures.

☐ 0.1 mg/mouse
+ 0.2 mg/mouse
○ 0.4 mg/mouse
◇ 0.8, 1.6, 4 mg/mouse

DETAILED DESCRIPTION OF PREFERRED EMBODIMENTS

The present invention contemplates a method of immunomodulatory therapy in a mammal said method comprising administering to said mammal an immunomodulating effective amount of one or more components of the cell wall of *Mycobacterium* or a related organism or analogous components from another biological source or chemical equivalents of said components.

In one aspect, the present invention is directed to a method of preventing, delaying onset of, curing or otherwise ameliorating the effects of an autoimmune disease in a mammal said method comprising administering to said mammal an autoimmune-preventing effective amount of one or more components of the cell wall of *Mycobacterium* or a related organism or analogous components from another biological source or chemical equivalents of said components.

In another aspect, the present invention provides a method of enhancing an immune response against melanoma or other cancer in a mammal said method comprising administering to said mammal an immunomodulatory effective amount of one or more components of the cell wall of *Mycobacterium* or a related organism or analogous components from another biological source or chemical equivalents of said components.

Autoimmune conditions contemplated by the present invention include but are not limited to IDDM, thyroiditis, atrophic gastritis (type A), pernicious anaemia, Addison's disease, pemphigus vulgaris, pemphigoid, multiple sclerosis, rheumatoid arthritis, systemic lupus erythematosus, discoid lupus erythematosus, haemolytic anaemia, sympathetic ophthalmia, uveitis, idiopathic thrombocytopenia, idiopathic leucopenia, primary biliary cirrhosis, autoimmune chronic active hepatitis, ulcerative colitis, Sjogren's syndrome, dermatomyositis, scleroderma and mixed connective tissue disease.

Cancers contemplated for immunomodulatory therapy include but are not limited to bladder cancer, carcinoma, melanoma amongst many others.

The present invention is hereinafter described in relation to IDDM but this is done with the understanding that the invention extends to autoimmune diseases such as contemplated above as well as the immunomodulatory therapy of cancers.

Accordingly, the present invention particularly contemplates a method of preventing, delaying onset of, curing, curing in association with islet replacement and/or pancreas transplant or otherwise ameliorating the effects of IDDM in a mammal said method comprising administering to said mammal an IDDM-preventing effective amount of one or more components of the cell wall of *Mycobacterium* or a related organism or analogous components from another biological source or chemical equivalents of said components.

The major components of the mycobacterial cell wall are: 1) mycolyl-arabinogalactan-peptidoglycan (MAPG), a polymer which provides the structural framework of the cell wall, 2) lipids, 3) phosphatidylinositol mannosides, and 4) lipoarabinomannan (LAM). MAPG has three major subdomains which are: 1) peptidoglycan, 2) arabinogalactan and 3) mycolic acids. N-acetylglucosaminyl-N-acetylmuramyl-L-alanyl-D-isoglutamine (GMDP) and N-acetylmuramyl-L-alanyl-D-isoglutamine (MDP) are peptidoglycan subunits considered to be responsible for most of the adjuvant activity of CFA.

Figure 1:
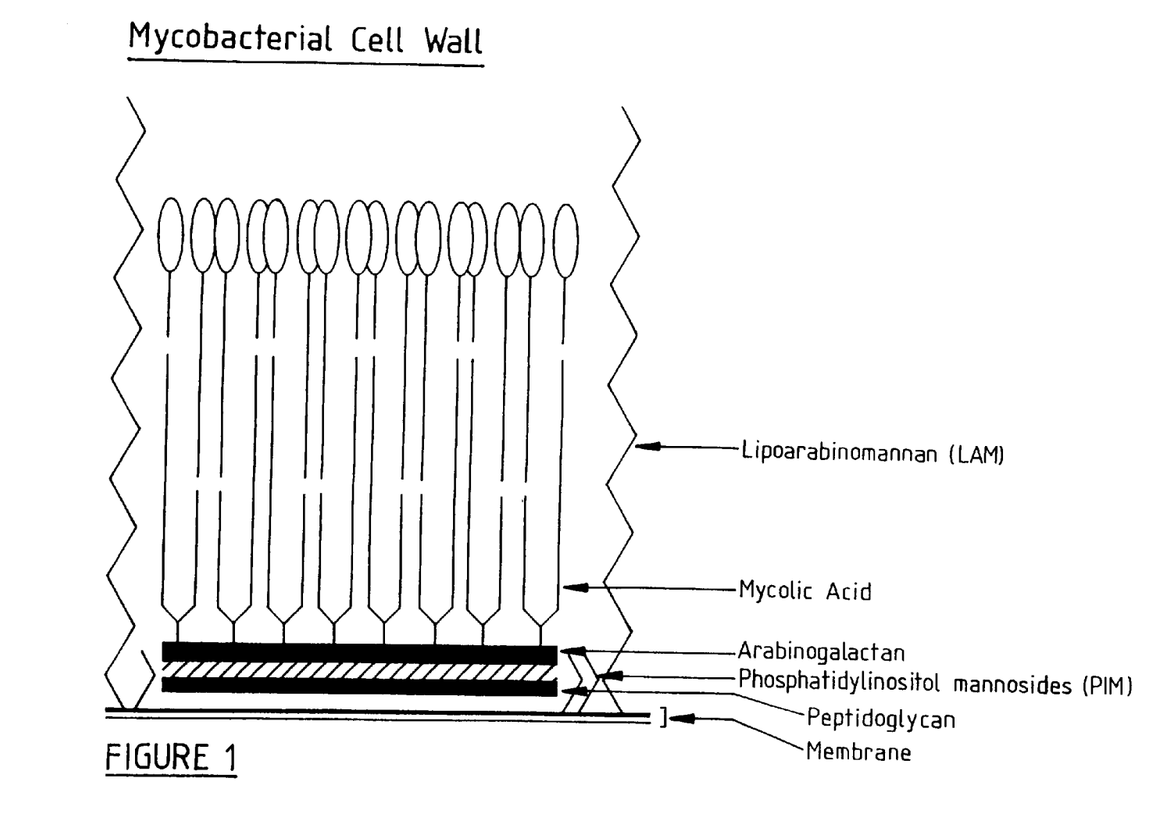
FIG. 1 is a diagrammatic representation of a mycobacterial cell wall.

The components of the *Mycobacterium* cell wall or of another suitable source or their chemical equivalents contemplated for use in preventing IDDM in mammals include MAPG or components or chemical equivalents thereof with or without other associated cell wall components and submolecular components or such as but not limited to mycolate, arabinogalactan and/or peptidoglycan or derivatives or chemical equivalents thereof (see FIG. 1). MAPG or its components may be in native or chemically synthetic form. MAPG is a complex of covalently attached macromolecules. Mycolic acids are covalently attached to arabinogalactan which is in turn covalently attached to peptidoglycan. Reference herein to "MAPG" includes the MAPG complex isolated from *Mycobacterium* or related organism or other suitable biological source or to a chemically or functionally equivalent complex as well as submolecular components including mycolic acids, peptidoglycan or arabinogalactan or chemical or functional equivalents thereof. The submolecular components may be in isolated form or in partial complex forms such as comprising mycolic acids and arabinogalactan, arabinogalactan and peptidoglycan or mycolic acids and peptidoglycan or chemical or functional equivalents thereof. A particular complex may also comprise, for example, mycolic acids covalently linking to arabinogalactan and this may in turn be covalently linked to a portion or derivative of peptidoglycan.

A convenient source of MAPG or its components is *Mycobacterium bovis* or BCG. The present invention, however, extends to MAPG or its components from any species of *Mycobacterium* or from physiologically, genetically, biochemically or structurally related microorganisms. Examples of similar organisms include *Actinomycetes*, *Nocardia* and *Corynebacterium*. A similar molecule or natural complex or components thereof may also be isolatable for other biological sources such as plants and coral. The MAPG complex or its components may be isolated from mycobacterial cell envelopes prepared, for example, by the method of Azuma et al (8).

According to this aspect of the present invention, there is provided a method for isolating components of MAPG for use in a therapeutic composition for preventing, delaying the onset of or otherwise ameliorating the effects of diabetes in a mammal, said method comprising preparing cell envelopes from a species of *Mycobacterium* or related organism or other suitable biological source, subjecting said cell envelopes to glycolipid removing means to remove soluble glycolipids, treating the product so obtained to break the mycolic acids linkage and isolating said mycolic acids, treating the remaining complex to cleave linkage at rhamnose residue connecting arabinogalactan to the peptidoglycan backbone and separating and isolating arabinogalactan and peptidoglycan.

The soluble glycolipids are conveniently removed by repeated centrifugation in the presence of sodium dodecyl sulphite (SDS). The resulting insolvent envelope MAPG complex is then subjected to fractionation.

The mycolic acids linkage is preferably cleaved by saponification, base-catalysed methanolysis or ammonolysis. The remaining complex of arabinogalactan and peptidoglycan is preferably then subjected to a Smith degradation comprising periodate followed by borohydride reduction and mild acid treatment.

The MAPG complex or its component parts or derivatives thereof may be in any convenient form such as vacuum-dried, powder, liquid or slurry.

The present invention further contemplates a composition of matter comprising MAPG or a derivative thereof or a component thereof or its derivative or chemical equivalents of MAPG or its components. These components are referred to herein as "active ingredients".

Preferably, the composition is a pharmaceutical composition for use in preventing, delaying onset of, curing, curing in association with islet replacement or otherwise ameliorating the effects of IDDM in mammals or for enhancing an anti-tumour immune response in mammals. The pharmaceutical composition may additionally comprise one or more pharmaceutically acceptable carriers and/or diluents.

According to this and other aspects of the present invention, preferred mammals include humans, primates, livestock animals (eg. cows, horses, sheep, pigs, donkeys), laboratory test animals (eg. mice, rabbits, guinea pigs, hamsters), companion animals (eg. dogs, cats) and captive wild animals (eg. kangaroos, foxes, deer).

The pharmaceutical forms suitable for injectable use include sterile aqueous solutions (where water soluble) and sterile powders for the extemporaneous preparation of sterile injectable solutions. The present invention also contemplates administration via topically applied compositions where molecules are used to permit entry via the skin. It must be stable under the conditions of manufacture and storage and must be preserved against the contaminating action of microorganisms such as bacteria and fungi.

The carrier may be a solvent medium containing, for example, water, ethanol, polyol (for example, glycerol, propylene glycol and liquid polyethylene glycol and the like) or suitable mixtures thereof and vegetable oils. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminummonostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying techniques which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with food material (including solid or liquid products). For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and about 2000 mg of active compound. Other ranges contemplated herein include from about 1 μg to about 1000 mg, from about 10 μg to about 100 mg and from about 100 μg to about 50 mg. Effective amounts may also be provided as an amount per kilogram of body weight of the recipient. For example, from about 0.01 ng to about 10,000 mg/kg body weight or may be administered from about 0.1 ng to about 500 mg/kg body weight.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Parental compositions may be administered by, for example, intravenous (IV), subcutaneous (SC) or intramuscular (IM) routes amongst other routes. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail. Other routes of administration are also contemplated by the present invention including intracerebral, intraperitoneal, intranasal, buccal, rectal, implant, infusion, inhalation administration in addition to intravenous drip.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 0.1 μg to about 2000 mg. Expressed in proportions, the active compound is generally present in from about 0.5 μg to about 2000 mg/ml of carrier. In the case of compositions containing supplementary active ingredients, the dosages are determined by reference to the usual dose and manner of administration of the said ingredients.

The active ingredients of the present invention may be administered alone or in combination with other therapeutic molecules such as molecules which reduce effects of the autoimmune pathology associated with IDDM. Alternatively, the active ingredients may be administered with anti-cancer agents or functionally unrelated but nevertheless useful molecules such as antibodies, analogues or the like. A single dose may be administered or multiple doses may be required with intervals of from minutes to hours, daily to weekly or monthly to yearly.

Reference herein to "preventing" IDDM includes total prevention of IDDM or substantial prevention for a limited time (eg. from about 1 to about 10 years) or delaying onset of IDDM or reducing the severity or otherwise ameliorating the effects of IDDM.

The present invention further contemplates use of a cell wall component of *Mycobacterium* in immunomodulatory therapy. Preferably, the therapy is the treatment of an autoimmune disease such as diabetes. Alternatively, the therapy is the treatment of melanoma, bladder cancer or other cancer, preferably by enhancing an immune response.

The present invention is further described by the following non-limiting Examples.

EXAMPLE 1

Components of Mycobacterial Cell Wall

Components of the mycobacterial cell wall are shown in FIG. 1.

EXAMPLE 2

Mice

Female NOD/Lt//Arc mice were obtained from the Animal Resources Centre (Canning Vale, WA, Australia) and maintained in clean conditions in the Centenary Institute Animal House. Sentinel mice were tested by serology at four-monthly intervals for the following pathogens: mouse hepatitis virus, rotavirus, ectomclia, mouse cytomegalovirus, polyoma virus, murine adenovirus, lymphocytic choriomeningitis virus, mouse pneumonia virus, retrovirus, Sendai virus, Theiler's murine encephalitis virus, *Bacillus piliformis, Mycoplasma pulmoniso, Bordetella bronchiseptica, Corynebacterium kutscheri, Klebsiella* species, *Pasturella multocide, Pasturella pneumotropica, Pseudomonas aeruginosa, Straphylococcus aureus, Streptococcus pneumoniae, Citrobacter freundii* and *salmonella* species. No mice tested positive for any of these pathogens. Mice were housed at 21 C and 40% humidity and were fed Barastock mouse chow (Melbourne, VIC, Australia) and acidified water ad libitum.

Under these conditions, about 75% of female NOD mice spontaneously developed IDDM by 35 weeks of age. The disease process involved a progressive preclinical phase of islet destruction which commenced at 4–6 weeks of age, and concluded with the onset of clinical diabetes between 14 and 35 weeks of age. Within a population, disease onset occurred in a sigmoidal fashion with the peak incidence of IDDM at 22 weeks of age, and a plateau at 35 weeks after which few previously unaffected mice ever progressed to diabetes (9).

NOD mice intravenously injected with a single dose of 1.0–4.0 mg of heat-killed BCG did not become diabetic, but developed a lupus-like disease characterised by haemolytic anaemia (indicated by a lowered haematocrit and positive Coombs' test), increased titres of anti-nuclear antibodies (demonstrated by immunofluorescence of HEp-2-cells) and glomerulonephritis (demonstrated by immunofluorescence of C3c bound to the renal glomeruli) (7).

EXAMPLE 3

BCG Therapy

Evans (Langhurst, UK) or CSL (Parkville, Australia) live freeze dried and attenuated *Mycobacterium bovis* (*bacillus* Calmette-Gucrin; BCG) vaccine was dissolved in isotomic saline and heat inactivated at 65 C for 45 minutes.

EXAMPLE 4

Mycobacterial Subfractions

Mannose-capped lipoarabinomannan (ManLAM) and mycolyl-abarbinogalactan-peptidoglycan complex (MAPG) may be prepared as previously described (8). N-acetylglucosaminyl-N-acetylmuramyl-L-alanyl-D-isoglutamine (GMDP) was purchased from a commercial source (GERBU Biotechnik, Gaibery, Germany). The Applicant acknowledges with appreciation receiving samples of ManLAM and MAPG from the Tuberculosis Repository by Drs P. J. Brennan and J. T. Belisle through NIAD13 November, 1996, NIH [Contract No. NO1-AU1-25147]. 0.

EXAMPLE 5

Random Blood Glucose Estimations

Each mouse was bled by retro-orbital venepuncture of 100–150 µl and the serum glucose concentration measured by the glucose oxidase technique on a Glucostix reagent strip (Ames, Basingstoke, UK). A mouse was considered to be diabetic if it was found to have a random blood glucose level >11.1 mMol/l.

EXAMPLE 6

Haematocrit Measurement

Seventy-five microlitres of blood were drawn up into a heparinized capillary tube (Becton Dickinson, Franklin Lakes, N.J., USA) and centrifuged at 1000 g for 15 minutes. The height of the column of packed red cells was divided by the total height of the column of blood and expressed as a percentage.

EXAMPLE 7

Direct Coombs Test

Mice were bled and the plasma removed. Ten microlitres of packed cells were resuspended in 5 ml PBS with 0.3% w/v bovine serum albumin, washed and resuspended in 1 ml of the same solution. Triplicates of 100 µl aliquots were placed in 96 well round bottom plates (Nunc, Denmark) with 3 serial ½ dilutions. The plates were vortexed and incubated at 37 C for 1 hr. Wells were then assessed for false positive results. Ten microlitres of 10 µg/ml polyclonal goat anti-mouse IgG (Sigma Chemical Company, MO, USA) added. Plates were then vortexed gently and incubated at 37 C for a further two hours. Wells in which the cells collected in a button were recorded as negative, while those in which the cells remained spread of the surface over the surface of the well were recorded as positive.

EXAMPLE 8

Assessment of Antinuclear Antibodies

Sera were assessed for binding to HEp-2 slides (Quantafluor, Chaska, Minn., USA). Slides were incubated in phosphate buffered saline (PBS) for 10 minutes. Sera diluted in PBS (starting concentration 1:100) were incubated on the slides at room temperature (RT) for 30 minutes in a moist chamber. Slides were then washed 3 times for 5 minutes in PBS and incubated for 30 minutes at RT with 1:50 FITC conjugated rat anti-mouse Ig (Serotec, Oxford, UK). Slides were again washed 3 times for 5 minutes with PBS, mounted and examined on an Axiophot fluorescence microscope (Zeiss, DDR). Sera from MRL/lpr-lpr and BALB/c mice were used as controls.

EXAMPLE 9

Detection of Glomerular Immune Complex Deposits

Kidneys were embedded in Tissue-Tek OCT Compound (Miles, Elkhart, IN) and frozen for histological analysis. Sections of 6 µm were cut on a Microm cryostat (Waldorf, Germany) and mounted on microscope slides, air dried, acetone fixed for 10 minutes and stored at −80 C in an air-tight bag containing silica desiccant. When slides were stained, they were thawed to room temperature, fixed in acetone for a further five minutes and blocked with 4% v/v foetal calf serum (FCS; CSL, Melbourne, VIC, Australia). Sections were stained with Goat anti-mouse C3c polyclonal IgG (Nordic Immunological Laboratories, Tilburg, Holland) at a 1:10 dilution in PBS for 45 minutes. Slides were then washed three times in PBS, and coverslipped with polyvinyl alcohol mounting media (Sanofi Diagnostics Pasteur Inc., Chaska, Minn.) and examined on a Leica fluorescence microscope (Leica Mikoskopie, Postfach, Germany).

EXAMPLE 10

Effects of Heat Killed BCG on Incidence of Diabetes

Figure 2:
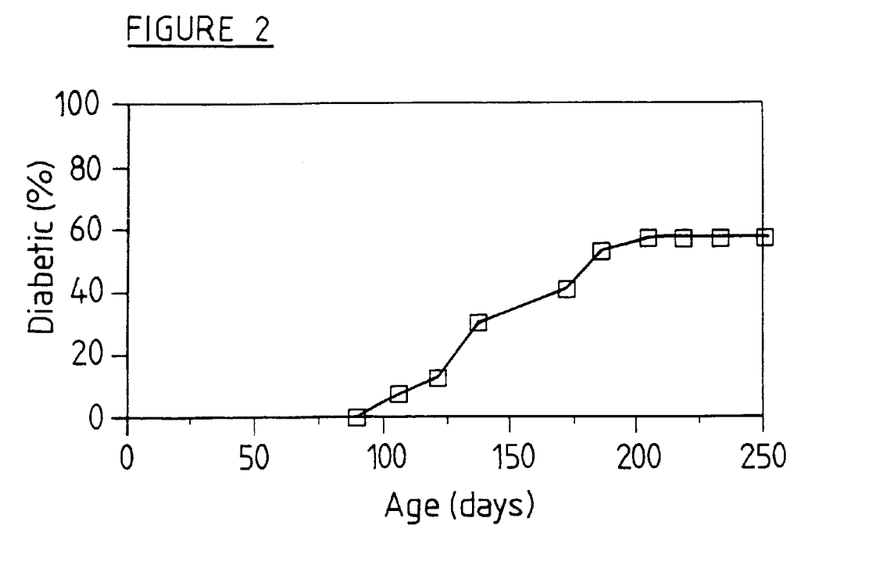
FIG. 2 is a graphical representation showing the percentage incidence of diabetes over time (days) following administration of phosphate buffered saline (PBS).
Figure 3:
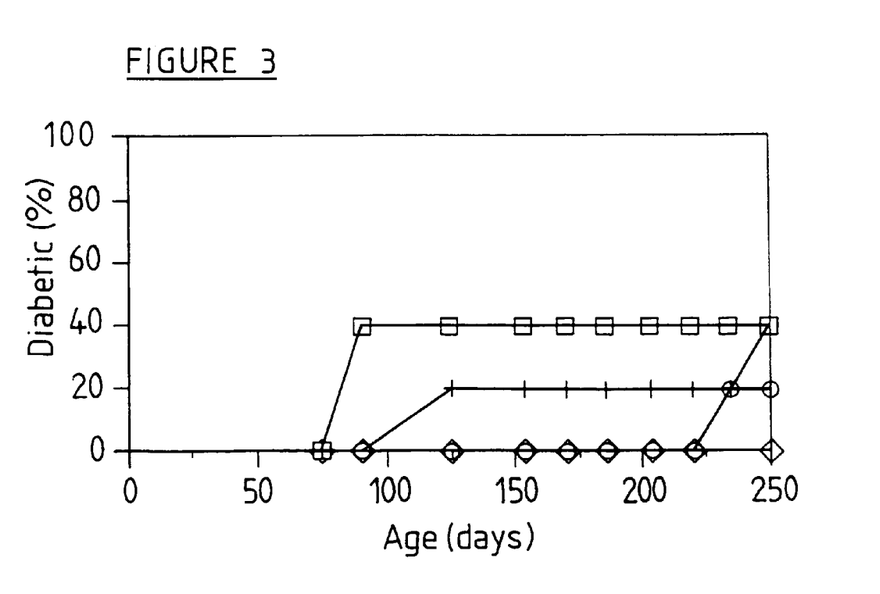
FIG. 3 is a graphical representation showing the percentage incidence of diabetes over time (days) following administration of BCG.
Figure 4:
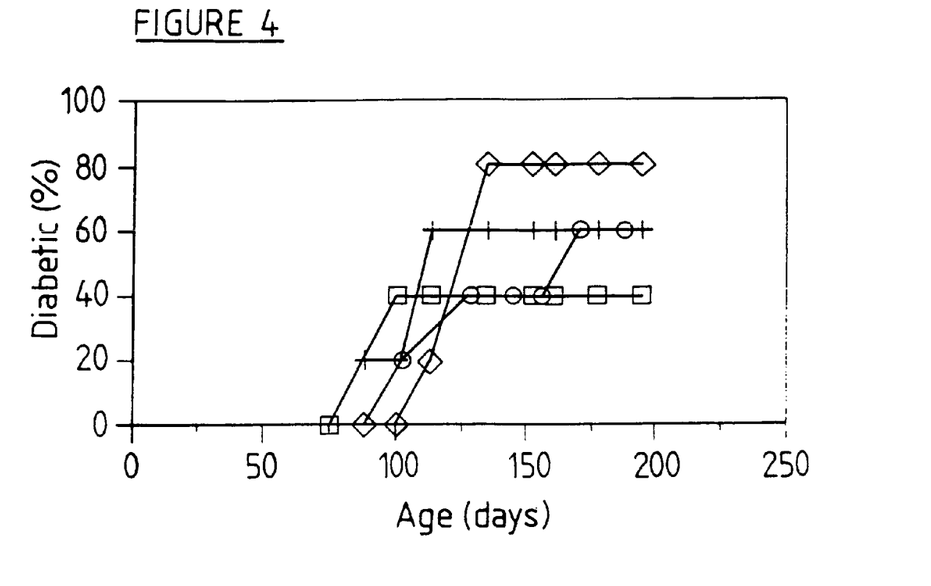
FIG. 4 is a graphical representation showing the percentage incidence of diabetes over time (days) following administration of N-CFAglucosaminyl-N-acetylmuramyl-L-alanyl-D-isoglutamine I.V. (1.0–10 μg).
□ 1.0 μg/mouse
+ 2.5 μg/mouse
○ 5.0 μg/mouse
◇ 10 μg/mouse
Figure 5:
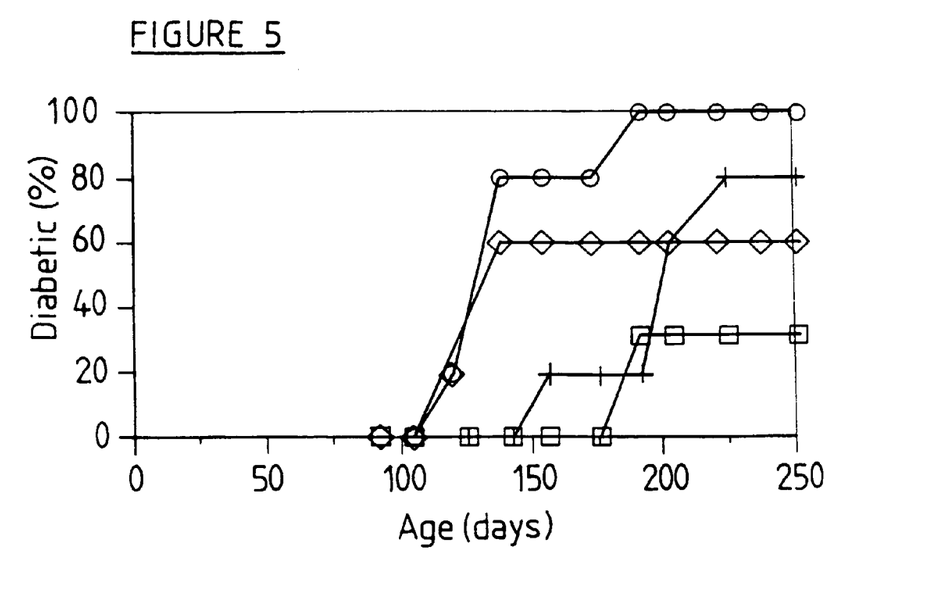
FIG. 5 is a graphical representation showing the percentage incidence of diabetes over time (days) following administration of lipoarabinomannan (6.25–50 μg I.V.).
□ 6.25 μg/mouse
+ 12.5 μg/mouse
○ 25 μg/mouse
◇ 50 μg/mouse

Varying concentrations of heat killed *Mycobacterium bovis* (BCG) were administered intravenously to NOD mice at 0.1 mg, 0.2 mg, 0.4 mg, 0.8 mg, 1.6 mg, 4 mg relative to a control of phosphate buffered saline (PBS; FIG. 2). No diabetes was detected in mice given 0.8, 1.6 or 4 mg of BCG (FIG. 3). Doses of 0.1 mg, 0.2 mg and 0.4 mg were not completely effective although they did provide some protection.

EXAMPLE 11

Effects of Mycobacterial Cell Wall Components on Incidence of Diabetes

In order to attempt to separate the activity of BCG which prevented IDDM from that which precipitated lupus, the mycobacterial subfractions GMDP, MAPG and ManLAM were tested for these activities. GMDP (10, 5.0, 2.5 and 1.0 µg), ManLAM (50, 25, 12.5 and 6.25 µg), and MAPG (1.0, 0.5, 0.25 and 0.125 mg) were each suspended in saline and injected intravenously into eight week old female NOD mice. These doses of MAPG and ManLAM were based on estimates of the equivalent quantities in 1 mg of BCG, while the does of GMDP was based on that used for immunoadjuvant activity; 10 µl g being the maximum dose tolerated by mice. Groups of 5 mice were tested and the incidence of diabetes compared to 17 saline treated and 14 BCG treated control mice. The results are shown in FIGS. 2 to 7.

Figure 6:
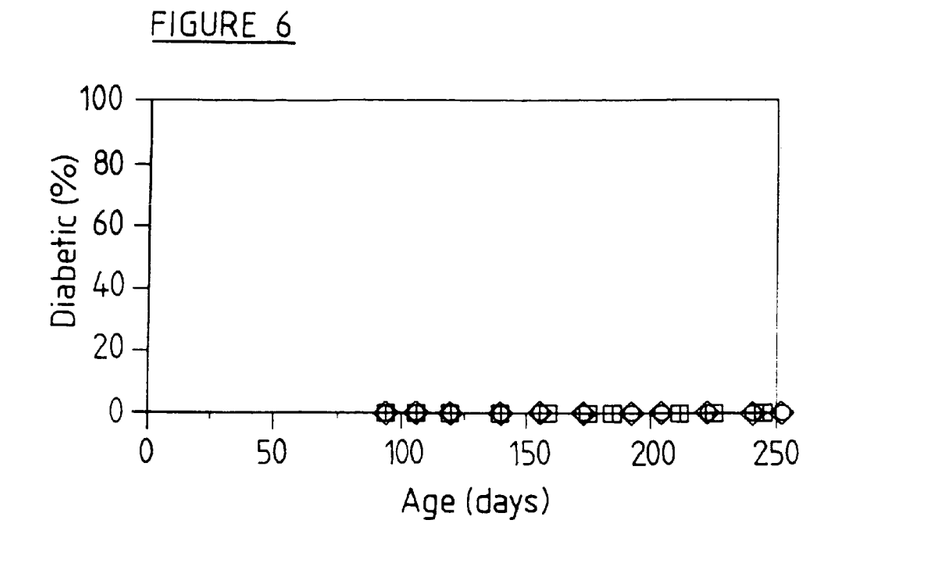
FIG. 6 is a graphical representation showing the percentage incidence of diabetes over time (days) following administration of mycolyl-arabinogalactan-peptidoglycan (0.125–1.0 mg I.V.).
□ 0.125 mg/mouse
+ 0.25 mg/mouse
○ 0.5 mg/mouse
◇ 1.0 mg/mouse
Figure 7:
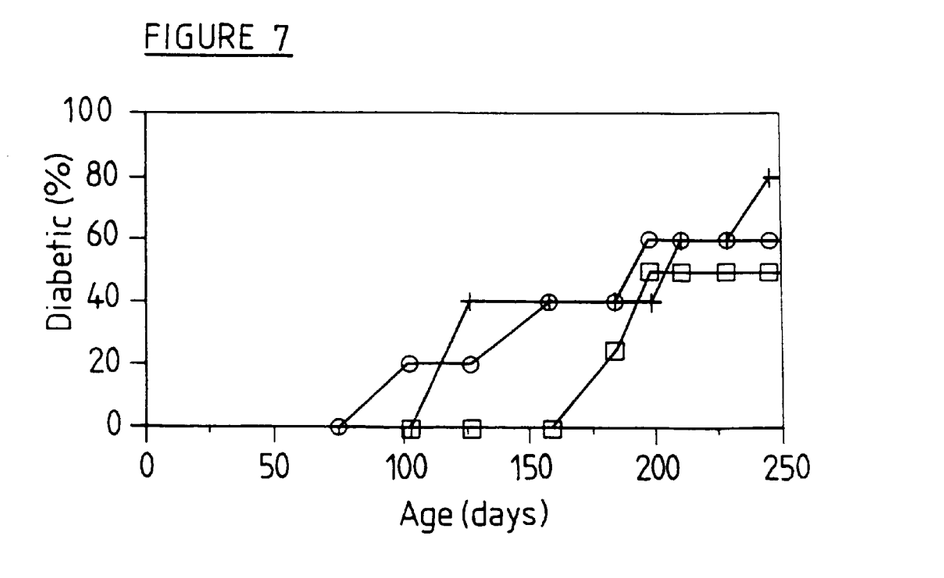
FIG. 7 is a graphical representation showing the percentage incidence of diabetes over time (days) following administration of mycolic acids (13–200 μg I.V.).
□ 12.5 μg/mouse
+ 50 μg/mouse
○ 200 μg/mouse.

While 10/17 (59%) PBS treated mice (FIG. 2), 12/20 (60%) of GMDP treated mice (FIG. 4) and 13/18 (72%) of ManLAM treated mice developed diabetes (FIG. 5) no mice receiving MAPG did so (FIG. 6). Haematocrits and Coombs' tests indicated that no mice receiving MAPG developed haemolytic anaemia whereas 11/14 (79%) of BCG treated (0.8–1.6 mg) control mice had a haematocrit below 46% and 7/14 mice were Coombs' test positive. Similarly there was no increase in the expression of antinuclear antibodies in the MAPG treated mice. The effects of mycolic acids administration on the incidence of diabetes is shown in FIG. 7.

EXAMPLE 12

Effects of Mycobacterial Cell Wall Components on Incidence of Diabetes

MAPG was injected intravenously into 8 week old NOD mice in doses ranging from 1 mg to 0.125 mg/mouse. All doses tested prevented IDDM. MAPG treated mice were tested for haematocrit, Coombs' test, antinuclear antibodies (ANA) and C3c complement component deposition in the renal glomeruli. No mice developed haemolytic anaemia as detected by lowered haematocrit and positive Coombs' test. ANA levels were not raised above those detected in PBS treated mice. Mild C3c deposition was found in a minority of mice. It was concluded that MAPG administration prevented IDDM without inducing lupus in NOD mice.

It is significant that while MAPG was still effective at preventing IDDM when used at a dose of 0.125 mg/mouse, BCG was ineffective at this dose. This indicates that it is likely that the effect of the MAPG preparation used in these experiments is due to MAPG itself and not to a contaminant from BCG.

EXAMPLE 13

Purification of Components of MAPG

*Mycobacterium* cell envelopes maybe prepared by the method of Azuma et al (8) and the soluble glycolipids removed by repeated centrifugation in the presence of SDS. The insoluble envelope component, the peptidoglycan conjugated with mycolic acids-substituted arabinogalactan, is fractionated into its constituent domains by the following procedure.

1. the mycolic acids linkage is cleaved by saponification, base-catalysed methanolysis or ammonolysis and separated from the insoluble residue.
2. the residue is submitted to Smith degradation (periodate, followed by borohydride reduction and mild acid treatment) to cleave the linkage at the rhamnose residue connecting the galactan to the peptidoglycan backbone.

Due to the nature of the furanosyl linkages in the galactan and arabinan domains, these residues are not affected by this treatment. The soluble arabinogalactan is separated from the peptidoglycan by centrifugation.

EXAMPLE 14

Testing Components of MAPG

The previous example shows the effectiveness of MAPG in preventing development of diabetes relative to other components of the mycobacterial cell wall. The individual constituents of MAPG are purified according to Example 13 and tested at varying concentrations in NOD mice. The incidence of diabetes is then determined over time.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Bach, J. F. *Enclocrine Rev* 15: 516, 1994.
2. Honeyman, M. C. and Harrison L. C. *Springer Semn Immunopathol* 14: 253, 1993.
3. Makino S et al *Exp. Anim* 29: 1–13, 1980.
4. Kanazawa Y, et al *Diabetologia* 27: 113–115, 1984.
5. Harada M et al *Diabetes Res Cln Pract* 8: 85, 1990.
6. Sadelain M, W. J. et al *Diabetes* 39: 583, 1990.
7. Baxter, A. G. et al *Immunology* 83: 227–231, 1997.
8. Azuma, I. et al *J. Bacterol.* 96: 1885–1887, 1968.
9. Baxter A. G. et al *Diabetes* 38: 1296–1300, 1989.

The invention claimed is:

1. A method of immunomodulatory treatment of insulin-dependent diabetes mellitus (IDDM) in a mammal said method comprising administering to said mammal an immunomodulating effective amount of mycolyl arabinogalactan peptidoglycan (MAPG), isolated from the cell wall of *Mycobacterium*.

2. The method according to claim 1, wherein said MAPG is administered with one or more of mycolic acids, peptidoglycan or arabinogalactan.

3. The method according to claim 1, wherein said MAPG is from *Mycobacterium bovis*.

4. The method according to claim 1, wherein the mammal is a human.

\* \* \* \* \*